(12) United States Patent
Ono et al.

(10) Patent No.: US 10,165,944 B2
(45) Date of Patent: Jan. 1, 2019

(54) CONTROL APPARATUS, CONTROL METHOD AND PROGRAM

(71) Applicant: CANON KABUSHIKI KAISHA, Tokyo (JP)

(72) Inventors: Shigeaki Ono, Tokyo (JP); Yukio Sakagawa, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 460 days.

(21) Appl. No.: 14/267,767

(22) Filed: May 1, 2014

(65) Prior Publication Data
US 2014/0327878 A1    Nov. 6, 2014

(30) Foreign Application Priority Data
May 2, 2013   (JP) ................................. 2013-096981

(51) Int. Cl.
*A61B 3/10* (2006.01)
*A61B 3/12* (2006.01)
*A61B 3/14* (2006.01)

(52) U.S. Cl.
CPC .............. *A61B 3/12* (2013.01); *A61B 3/102* (2013.01); *A61B 3/145* (2013.01)

(58) Field of Classification Search
CPC .......... A61B 3/00; A61B 3/12; A61B 3/1208; A61B 3/102; A61B 3/145

USPC ......................................................... 351/206
See application file for complete search history.

(56) References Cited

U.S. PATENT DOCUMENTS

2009/0257065 A1* 10/2009 Hauger ................. A61B 3/102
356/479

FOREIGN PATENT DOCUMENTS

| JP | 2008-154704 A | 7/2008 |
| JP | 2011147609 A | 8/2011 |

OTHER PUBLICATIONS

Cirrus HD-OCT User Manual. Carl Zeiss Meditec, 2009.*
Adobe Photoshop CS3 User Guide. Adobe Systems Incorporated, 2007.*

* cited by examiner

*Primary Examiner* — Jie Lei
*Assistant Examiner* — Mitchell Oestreich
(74) *Attorney, Agent, or Firm* — Canon U.S.A., Inc. IP Division

(57) ABSTRACT

In an eye fundus surface expansion observation screen, a surface moving image that is a moving image showing the surface of a predetermined region in a subject's eye is enlarged and displayed. In an eye fundus tomography expansion confirmation screen, a tomographic image showing the tomography of the subject's eye, which corresponds to a position selected from the surface moving image, is enlarged and displayed.

19 Claims, 4 Drawing Sheets

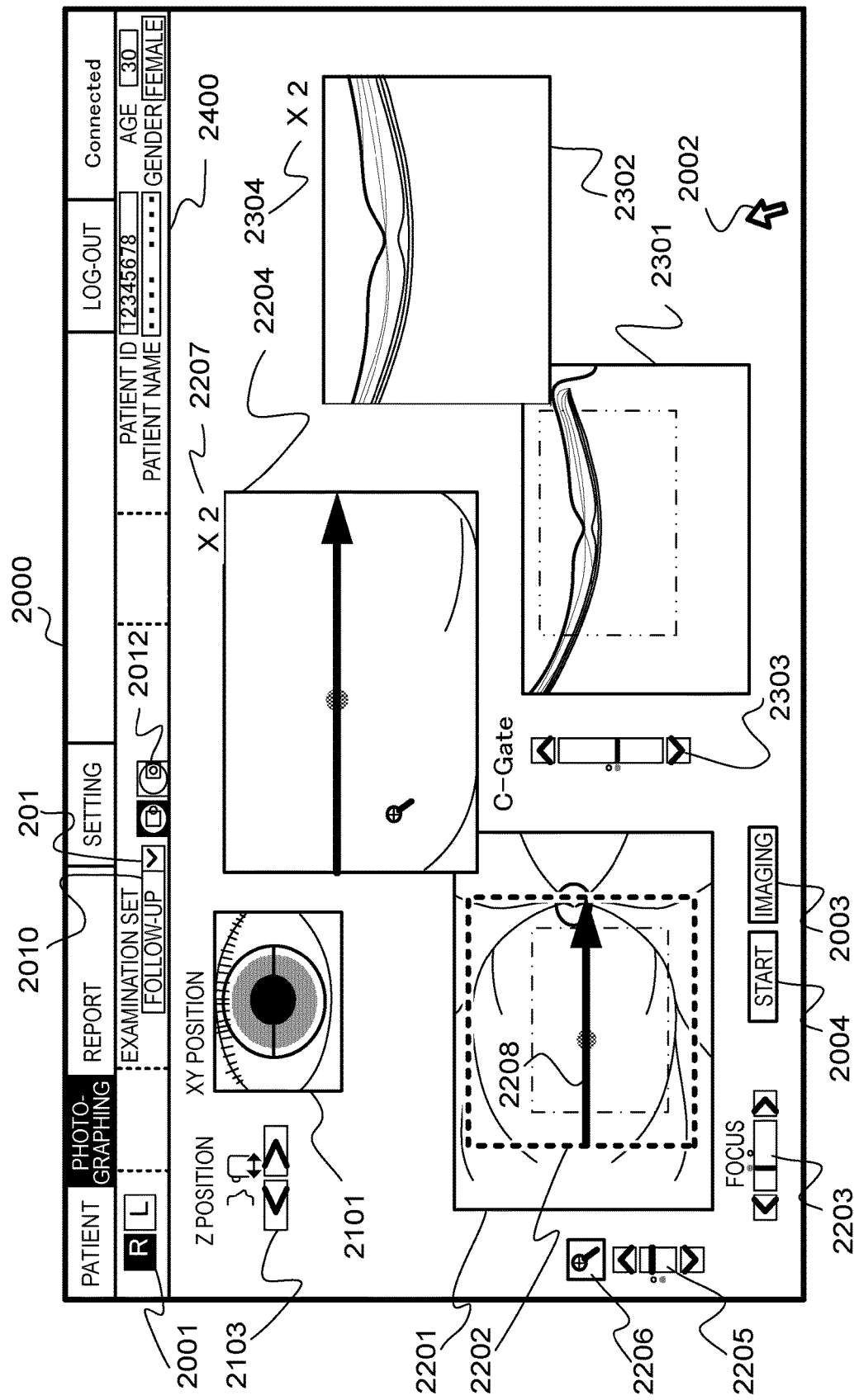

CONTROL APPARATUS, CONTROL METHOD AND PROGRAM

BACKGROUND OF THE INVENTION

Field of the Invention

The present invention relates to a technique of acquiring a tomographic image of an examination object.

Description of the Related Art

Currently, as an ophthalmological apparatus using optical equipment, various things such as an anterior eye part imaging apparatus, an eye fundus camera, and a scanning laser ophthalmoscope (SLO) are used. Especially, an optical tomographic image imaging apparatus (hereafter referred to as "OCT apparatus") by an optical coherence tomography (OCT) using multi-wavelength light wave interference can acquire tomographic image data of a sample at high resolution, which is becoming an essential ophthalmological apparatus in special outpatient clinics of the retinae.

Japanese Patent Application Laid-Open No. 2008-154704 discloses a technique that can arrange and display eye fundus surface image data showing an eye fundus surface and eye fundus tomographic image data showing an eye fundus tomogram.

SUMMARY OF THE INVENTION

The control apparatus of the present invention includes:

an acquiring unit configured to acquire a surface moving image that is a moving image showing a surface of a predetermined region in an examination object;

a display control unit configured to display the acquired surface moving image on a displaying unit; and a display magnification control unit configured to control a display magnification of the surface moving image, in which the display control unit displays a tomographic image that is a moving image showing a tomography of the examination object, which corresponds to a position selected from the surface moving image in the controlled display magnification, on the displaying unit.

Further features of the present invention will become apparent from the following description of exemplary embodiments (with reference to the attached drawings).

BRIEF DESCRIPTION OF THE DRAWINGS

FIGS. 2A & 2B are diagrams illustrating a screen example displayed in an ophthalmological apparatus according to an embodiment of the present invention.

DESCRIPTION OF THE EMBODIMENTS

Normally, in the case of imaging eye fundus tomographic image data, a lesion area of the subject eye is confirmed by eye fundus surface image data and the eye fundus tomographic image data is imaged with respect to the lesion area. However, since the high resolution of the OCT apparatus has been improved, the display magnification at the time of observing the eye fundus surface image data is not considered in the related art. Therefore, in a case where a small lesion area is targeted, when the display magnification of eye fundus surface image data is fixed, it is difficult to determine the lesion area and it is not possible to easily decide the position of imaged eye fundus tomographic image data. As a result, there is a problem of taking time to image the eye fundus tomographic image data or requiring the reacquisition of the eye fundus tomographic image data, that is, placing a burden on the subject.

Therefore, it is an object of a control apparatus according to the present embodiment to be able to easily and accurately set the position of a tomographic image of an examination object to be imaged. Therefore, it includes a display control unit configured to display a surface moving image that is a moving image showing the surface of a predetermined region in an examination object on a displaying unit. Moreover, the control apparatus according to the present embodiment includes a display magnification control unit configured to control the display magnification of the surface moving image. Moreover, the display control unit according to the present embodiment displays a tomographic image that is a moving image showing the tomography of the examination object, which corresponds to a position selected from the surface moving image in the controlled display magnification, on the displaying unit. By this means, it is possible to easily and accurately set the position of the tomographic image of the examination object to be imaged.

In the following, a preferred embodiment to which the present invention is applied is described in detail with reference to the accompanying drawings.

<Configuration of Ophthalmological Apparatus>

Figure 1A:
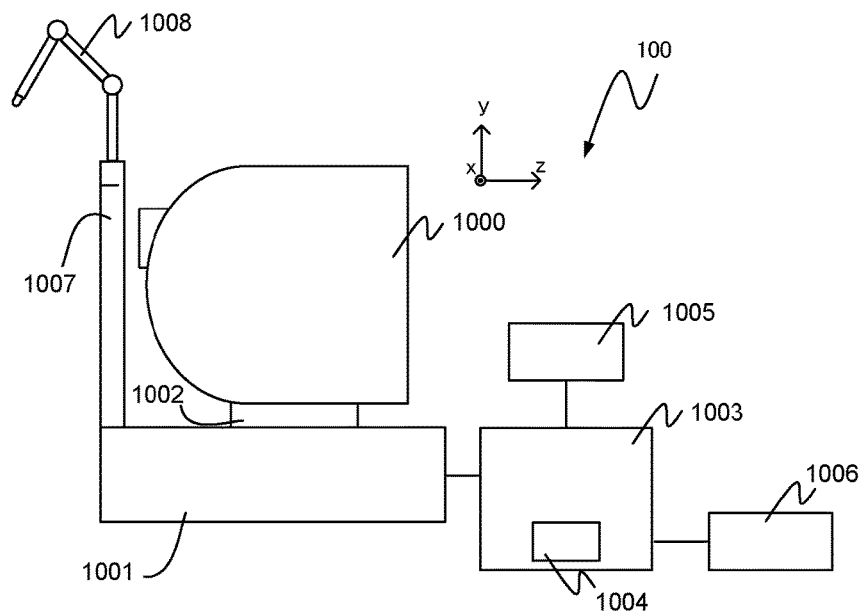
FIGS. 1A & 1B are diagrams illustrating a configuration of an ophthalmological apparatus according to an embodiment of the present invention.
Figure 1B:
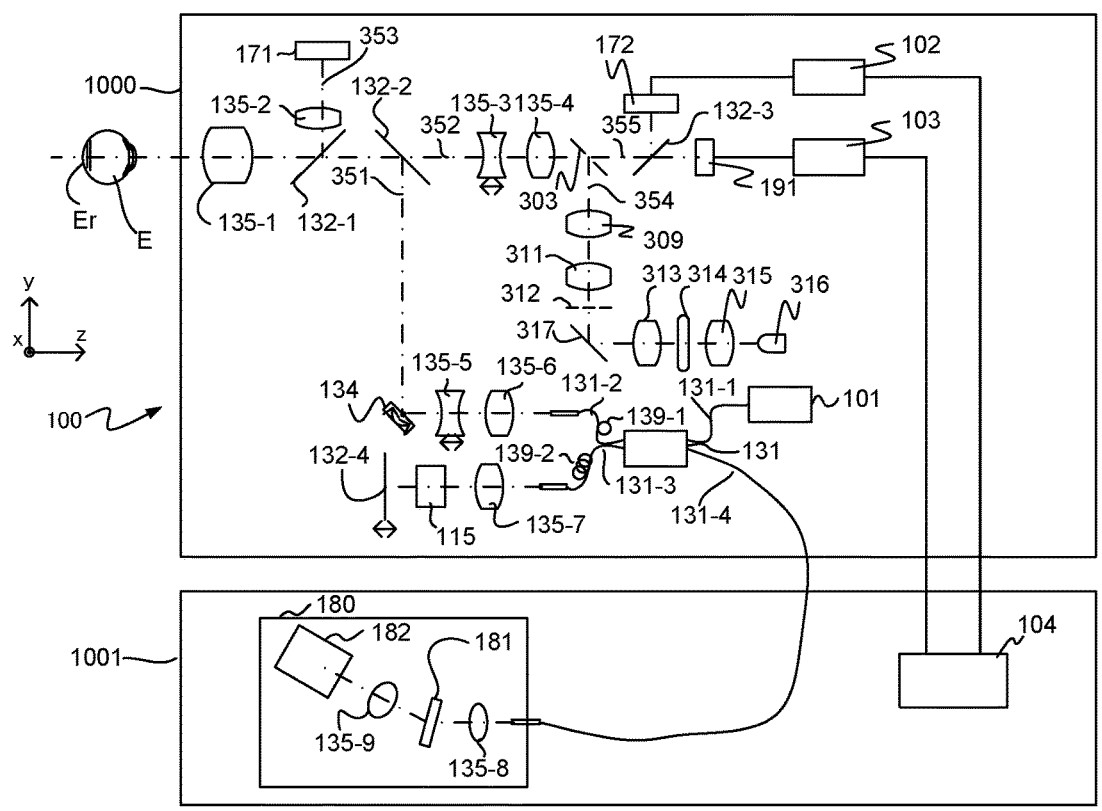

FIG. 1 is a diagram illustrating the configuration of an ophthalmological apparatus according to an embodiment of the present invention. That is, FIG. 1A illustrates the appearance configuration of the ophthalmological apparatus according to the present embodiment and FIG. 1B illustrates the internal configurations of an optical head and base unit of the ophthalmological apparatus according to the present embodiment. Here, the ophthalmological apparatus illustrated in FIG. 1 has a configuration as a control system example.

In FIG. 1A, reference numeral 100 indicates an ophthalmological apparatus. Reference numeral 1000 indicates an optical head that is a measurement optical system to image anterior eye part surface image data showing the surface of an anterior eye part, eye fundus surface image data showing the surface of an eye fundus, and eye fundus tomographic image data showing the tomogram of the eye fundus. Reference numeral 1002 indicates a stage portion to move the optical head 1000 in the xyz directions in FIG. 1A by the use of a motor which is not illustrated. Reference numeral 1001 indicates a base portion incorporating a spectroscope described below.

Reference numeral 1003 indicates a computer that controls the movement processing of the optical head 1000 by the stage portion 1002 and controls the imaging processing of eye fundus tomographic image data. Reference numeral 1004 indicates a hard disk that is built into the computer 1003 and stores subject information and a program to image the eye fundus tomographic image data, and so on. Reference numeral 1005 indicates a monitor as a displaying unit. Reference numeral 1006 indicates an input portion by which an examiner gives an instruction to the computer 1003, and is specifically configured with a keyboard and a mouse. Reference numeral 1007 indicates a jaw stand or an external fixation lamp that urges the fixation of the eyes of the subject (subject's eyes) by fixing the jaw and forehead of the subject, and is used for visual fixation of the eyes of the subject. Here, the computer 1003 has a configuration as a control apparatus example.

<Configurations of Measurement Optical System and Spectroscope>

Next, the internal configurations of the optical head 1000 and the base portion 1001 are described with reference to FIG. 1B. First, the internal configuration of the optical head 1000 is described. An objective lens 135-1 is installed facing subject's eye E, and, depending on each wavelength band range, diverges into an optical path 351 of the OCT optical system, an optical path 352 for eye fundus observation and fixation lamp and an optical path 353 for anterior eye part observation by a first dichroic mirror 132-1 and a second dichroic mirror 132-2 on the optical axis. Here, reference numerals 135-3 and 135-4 indicate lenses, and the lens 135-3 is driven by an unillustrated motor for the focus adjustment of a fixation lamp 191 and an eye fundus observation CCD 172.

A perforated mirror 303 is arranged between the lens 135-4 and a third dichroic mirror 132-3, and the optical path 352 diverges into an optical path 355 and an optical path 354. The optical path 354 forms an illumination optical system that illuminates the eye fundus of subject's eye E, in which an LED light source 316 that is an illumination light source for eye fundus observation used for the position adjustment of subject's eye E and a stroboscopic tube 314 used to image eye fundus image data of subject's eye E are installed. Reference numerals 313 and 315 indicate condenser lenses and reference numeral 317 indicates a mirror. The illumination light from the LED light source 316 and the stroboscopic tube 314 becomes a ring-shaped light flux by a ring slit 312, is reflected by the perforated mirror 303 and illuminates retina Er of subject's eye E. Here, reference numerals 309 and 311 indicate lenses. The LED light source 316 uses about 780 nm as the center wavelength.

After the perforated mirror 303 on the optical path 352, depending on each wavelength band range, it is diverged into an optical path to the eye fundus observation CCD 172 and an optical path to the fixation lamp 191 by the third dichroic mirror 132-3. The eye fundus observation CCD 172 has the sensibility near the center wavelength (780 nm) of the LED light source 316 that is an illumination light for eye fundus observation, and is connected with a CCD control unit 102. On the other hand, the fixation lamp 191 causes visible light to urge the fixation of the subject, and is connected with a fixation lamp control unit 103.

The CCD control unit 102 and the fixation lamp control unit 103 are connected with a calculation unit 104, and exchange data between the base portion 1001 and the computer 1003 through the calculation unit 104. In the optical path 353, reference numeral 135-2 indicates a lens and reference numeral 171 indicates a CCD for anterior eye observation. The anterior eye part observation CCD 171 has the sensibility near the wavelength (970 nm) of illumination light for anterior eye observation which is not illustrated. Moreover, an unillustrated image split prism is arranged in the optical path 353, and it is possible to detect the distance in the z direction of the optical head 1000 with respect to subject's eye E, as a split image in the anterior eye observation image.

The optical path 351 forms an OCT optical system and images eye fundus tomographic image data of eye fundus Er of subject's eye E. To be more specific, the optical path 351 acquires an interference signal to form the eye fundus tomographic image data. Reference numeral 134 indicates an XY scanner to scan light on the eye fundus. Although the XY scanner 134 is illustrated as one mirror, it performs scanning in the biaxial direction of XY. Reference numerals 135-5 and 135-6 indicate lenses, where the lens 135-5 is driven by an unillustrated motor to perform focus adjustment of light of a light source 101, which is emitted from a fiber 131-2 connected with an optical coupler 131, on eye fundus Er. By this focus adjustment, light from an eye fundus 107 is formed in a spot shape and entered into the leading edge of the fiber 131-2 at the same time.

Next, the optical path from the light source 101 and the configurations of a reference optical system and a spectroscope are described. In FIG. 1B, reference numeral 101 indicates a light source. Reference numeral 132-4 indicates a mirror. Reference numeral 115 indicates glass for dispersion compensation. Reference numeral 131 indicates an optical coupler. Reference numerals 131-1 to 131-4 indicate single-mode optical fibers connected and integrated with the optical coupler. Reference numeral 135-7 indicates a lens. Reference numeral 180 indicates a spectroscope.

A Michelson interferometer is formed with the above-mentioned configuration. Light emitted from the light source 101 passes the optical fiber 131-1 and is divided into measurement light on the side of the optical fiber 131-2 and reference light of the optical fiber 131-3 through the optical coupler 131. The measurement light is irradiated to eye fundus Er of subject's eye E that is the observation object through the above-mentioned OCT optical system optical path, and reaches the optical coupler 131 by reflection or diffusion in the retina through the same optical path.

On the other hand, the reference light reaches the mirror 132-4 through the optical fiber 131-3, the lens 135-7 and the dispersion compensation glass 115 inserted to adjust the dispersion of the measurement light and the reference light, and is reflected. Further, the reflected light returns to the same optical path and, reaches the optical coupler 131.

The measurement light and the reference light are multiplexed by the optical coupler 131 to become interference light. Here, interference is caused when the optical path length of the measurement light and the optical path length of the reference light become almost identical. The mirror 132-4 is held so as to adjustable in the optical axis direction by an unillustrated motor and driving mechanism, and can adjust the optical path length of the reference light to the optical path length of the measurement light that changes by subject's eye E. The interference light is led to the spectroscope 180 through the optical fiber 131-4.

"139-1" indicates a polarization adjustment unit on the measurement light side which is installed in the optical fiber 131-2. "139-2" indicates a polarization adjustment unit on the reference light side which is installed in the optical fiber 131-3. These polarization adjustment units have some parts in which the optical fibers are drawn in a loop manner, and can adjust and match the polarization states of the measurement light and the reference light by rotating these loop-shaped parts with respect to the longitudinal direction of the fibers and adding a twist to the fibers. Here, in the present embodiment, it is assumed that the polarization states of the measurement light and the reference light are adjusted and fixed in advance.

The spectroscope 180 is formed with a lens 135-8, a lens 135-9, a diffraction lattice 181 and a line sensor 182. After the interference light emitted from the optical fiber 131-4 becomes substantially parallel light through the lens 135-8, it is dispersed by the diffraction lattice 181 and formed in the line sensor 182 by the lens 135-9.

Next, the light source 101 is described. The light source 101 is an SLD (Super Luminescent Diode) that is a representative low coherent source. The center wavelength is 855 nm and the wavelength bandwidth is about 100 nm. Here, the bandwidth is an important parameter because it influences the resolution in the optical axis direction of an acquired topographic image. Moreover, although the SLD is selected here as the light source type, it only has to emit low coherent light, and it is possible to use ASE (Amplified Spontaneous Emission), and so on. Taking into account the eye measurement, near-infrared light is suitable as the center wavelength. Moreover, since the center wavelength influences the resolution in the horizontal direction of an acquired tomographic image, it is desirable to be a shorter wavelength as much as possible. The center wavelength is set to 855 nm for both reasons.

Although a Michelson interferometer has been used as an interferometer in the present embodiment, a Mach-Zehnder interferometer may be used. It is preferable to use the Mach-Zehnder interferometer in a case where the light quantity difference between measurement light and reference light is large, and use the Michelson interferometer in a case where the light quantity difference is relatively small.

<Imaging Screen>

Figure 2A:
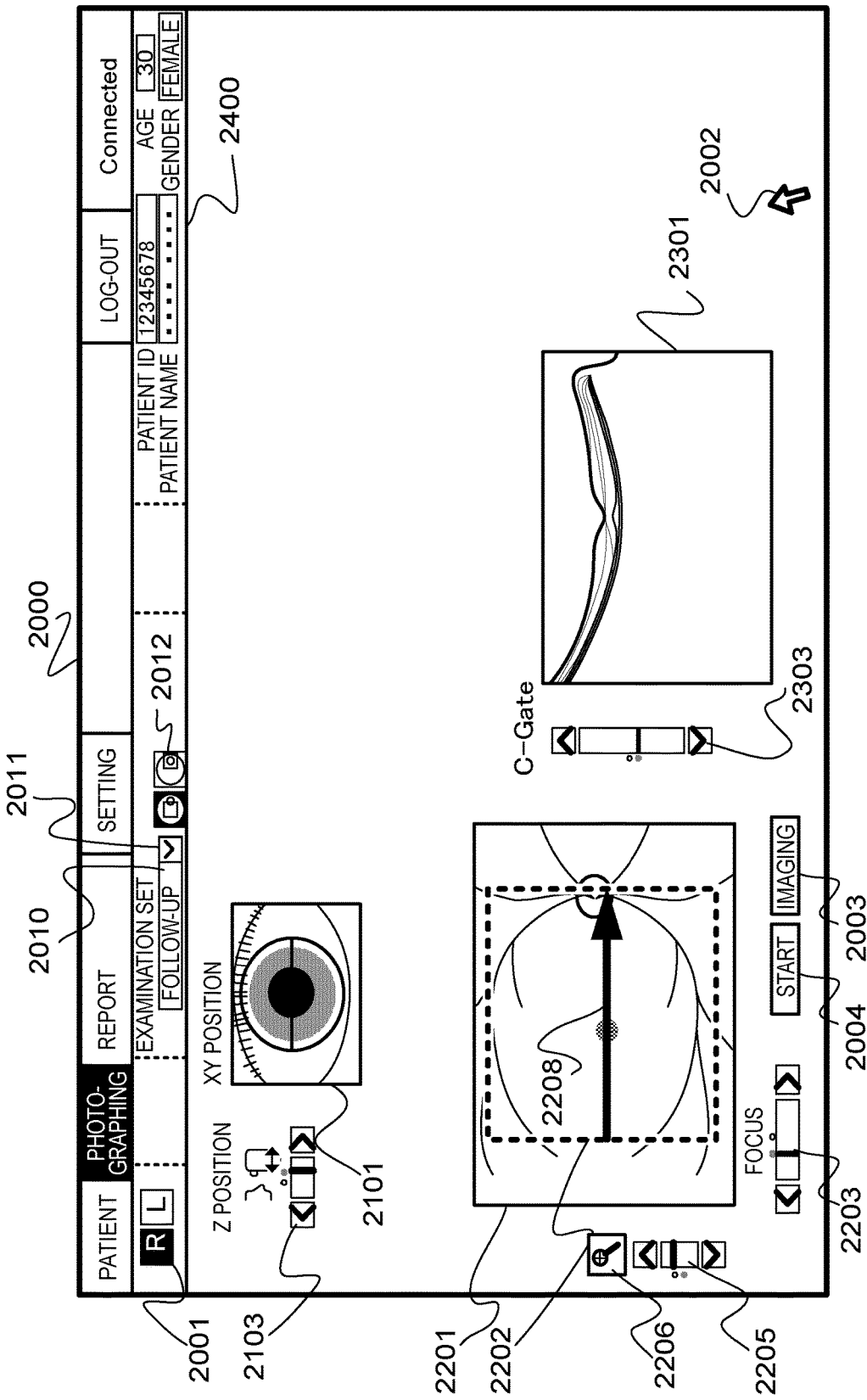

Next, an imaging screen in the present embodiment is described with reference to FIG. 2A. In FIG. 2A, reference numeral 2000 indicates the imaging screen. An imaging screen 2000 is a screen to perform various settings and adjustment to acquire a desired subject's eye image, and is displayed on the monitor 1005 before an image is taken.

In FIG. 2A, reference numeral 2400 indicates a patient information displaying unit that displays various kinds of information on the patient who is currently examined (for example, patient ID, patient name, age and sex). Reference numeral 2101 indicates an anterior eye part observation screen to display anterior eye part surface image data acquired by the anterior eye part observation CCD 171. Reference numeral 2201 indicates an eye fundus surface observation screen to display eye fundus surface image data (surface moving image) acquired by the eye fundus observation CCD 172. Reference numeral 2301 indicates an eye fundus tomography confirmation screen to confirm the eye fundus tomographic image data (tomographic moving image). Reference numeral 2001 indicates a button that switches the right and left of the subject's eye, and, by pressing the "L" or "R" button, the optical head 1000 moves to the initial position of the right or left eye.

Reference numeral 2010 indicates an examination set selection screen that displays a selected examination set. The examination set denotes a scan pattern group that stores at least one scan pattern together with the order. Examples of the examination set include a scan pattern group suitable for macular disease, a scan pattern group suitable for glaucoma, and a scan pattern group suitable for papilla analysis or anterior eye part analysis. Moreover, there is also an examination set called "follow-up" having the same scan pattern group as at the time of imaging processing in the past. At the time of changing the examination set, the examiner displays an unillustrated pull-down menu by clicking a button 2011 and selects a desired examination set. Moreover, a scan pattern display screen 2012 sequentially displays the outline of a scan pattern performed by the currently selected examination set, such as a 3D scan and a cross scan.

Reference numeral 2002 indicates a mouse cursor, and the examiner moves the position of this mouse cursor by operating a mouse included in an input unit 929. An ophthalmological apparatus 100 includes a position detecting unit of the mouse cursor and is formed so as to change the alignment according to the position of the mouse cursor. The position detecting unit of the mouse cursor calculates the position from the pixel position on the display screen of the mouse cursor. A range is set in the measurement screen, and the association between the set range and the alignment drive is set in advance. By this means, when there is the mouse cursor in pixels within the set range, it is possible to perform alignment defined within the set range. Moreover, the alignment operation by the mouse is performed by rotating a mouse wheel.

Reference numeral 2004 indicates a start button, the acquisition of eye fundus tomographic image data and eye fundus surface image data is started by pressing the start button 2004, and each is displayed on the eye fundus tomography confirmation screen 2301 and the eye fundus surface observation screen 2201 in real time as a moving image. At this time, a frame 2202 displayed in the eye fundus surface observation screen 2201 shows a range in which the eye fundus tomographic image data is acquired in the eye fundus surface image data. Moreover, a cursor 2208 shown by a horizontal directional line indicates the position and scan direction on subject's eye E of the eye fundus tomographic image data displayed on the eye fundus tomography confirmation screen 2301, and can be moved by the mouse.

A slider 2103 arranged near the anterior eye part surface observation screen 2101 is a slider to adjust the position in the Z direction of the optical head 1000 with respect to subject's eye E. A slider 2203 arranged near the eye fundus surface observation screen 2201 is a slider to perform focus adjustment. Similarly, a slider 2205 arranged near the eye fundus surface observation screen 2201 is a slider to adjust the magnification of the eye fundus surface image data. A slider 2303 arranged near the eye fundus tomography confirmation screen 2301 is a slider to adjust a coherence gate.

Here, the above-mentioned focus adjustment denotes adjustment to move the lenses 135-3 and 135-5 in the direction illustrated in FIG. 1B in order to perform focus adjustment with respect to eye fundus Er. Moreover, the above-mentioned coherence gate adjustment denotes adjustment to move the mirror 132-4 in the direction shown by the arrow in FIG. 1B in order to observe the eye fundus tomographic image data in a desired position of the eye fundus tomography confirmation screen 2301. Moreover, these sliders 2103, 2203, 2205, and 2303 are designed to coordinate and move even at the time of alignment operation by the mouse in image data displayed on the corresponding screen.

Reference numeral 2206 indicates an expansion button to expand eye fundus surface image data displayed on the eye fundus surface observation screen 2201, and, after the expansion button 2206 is pressed, the magnification adjustment of the eye fundus surface image data is performed by the slider 2205. Reference numeral 2003 indicates an imaging button, and, by pressing the imaging button 2003 when various kinds of adjustment is finished, imaging processing of still image data showing the tomography of the eye fundus is performed.

Next, the imaging processing of eye fundus tomographic image data by the ophthalmological apparatus 100 according to the present embodiment is described. First, by pressing the start button 2004, the operator starts the acquisition of eye fundus surface image data that is moving image data.

In FIG. 1B, illumination light from the LED light source 316 passes the condenser lenses 315 and 313, is reflected by the mirror 317, becomes a ring-shaped light flux by the ring slit 312, passes the lens 311 and the lens 309, is reflected by the perforated mirror 303, passes the lens 135-3, the lens 135-4, the second dichroic mirror 132-2, the first dichroic mirror 132-1 and the objective lens 135-1 and illuminates retina Er of subject's eye E.

The reflected light from retina Er of subject's eye E passes the objective lens 135-1, passes the first dichroic mirror 132-1, the second dichroic mirror 132-2, the lens 135-3, the lens 135-4 and a hole part of the perforated mirror 303, is reflected by the third dichroic mirror 132-3 and formed in the CCD 172. The eye fundus surface image formed in the CCD 172 is read by the CCD control unit 102, amplified, subjected to A/D conversion and input in the calculation unit 104 as eye fundus surface image data. The eye fundus surface image data input in the calculation unit 104 is imported in the computer 1003 illustrated in FIG. 1A and thereby displayed in real time on the eye fundus surface observation screen 2201.

The computer 1003 performs contrast detection processing on the imported eye fundus surface image data, drives the lens 135-3 to a position in which the contrast of the eye fundus surface image data is the best, and performs focus adjustment with respect to eye fundus Er of subject's eye E. By controlling the XY scanner 134, the ophthalmological apparatus 100 can image the eye fundus tomographic image data of a desired region in eye fundus Er of subject's eye E.

First, measurement light is scanned in the x direction in FIG. 1B, and information of a given imaging number is imaged from an imaging range in the x direction in eye fundus Er by the line sensor 182. The eye fundus tomographic image data imaged by the line sensor 182 is imported in the computer 1003, and the luminance distribution on the line sensor 182, which is acquired in a given position in the x direction, is subjected to FFT processing. In order to show linear luminance distribution acquired by the FFT processing on the monitor 1005, the concentration or color information converted therefrom is referred to as "A scan image data". Two-dimensional image data in which these multiple items of A scan image data are arranged is referred to as "B scan image data". After multiple items of A scan image data to form one B scan image data are imaged, by moving the scan position in the y direction and performing scanning in the x direction again, multiple items of B scan image data are acquired.

By displaying the multiple items of B scan image data or three-dimensional eye fundus tomographic image data formed with the multiple items of B scan image data on the monitor 1005, the examiner can use it to diagnose subject's eye E. The acquired eye fundus tomographic image data of subject's eye E is displayed in real time on the eye fundus tomography confirmation screen 2301.

The computer 1003 detects the contrast of the imported eye fundus tomographic image data, drives the lens 135-3 to the position in which the contrast of the eye fundus tomographic image data is the best, and automatically performs focus adjustment with respect to eye fundus Er of subject's eye E.

<Eye Fundus Tomographic Image Data Imaging Processing>

Figure 3:
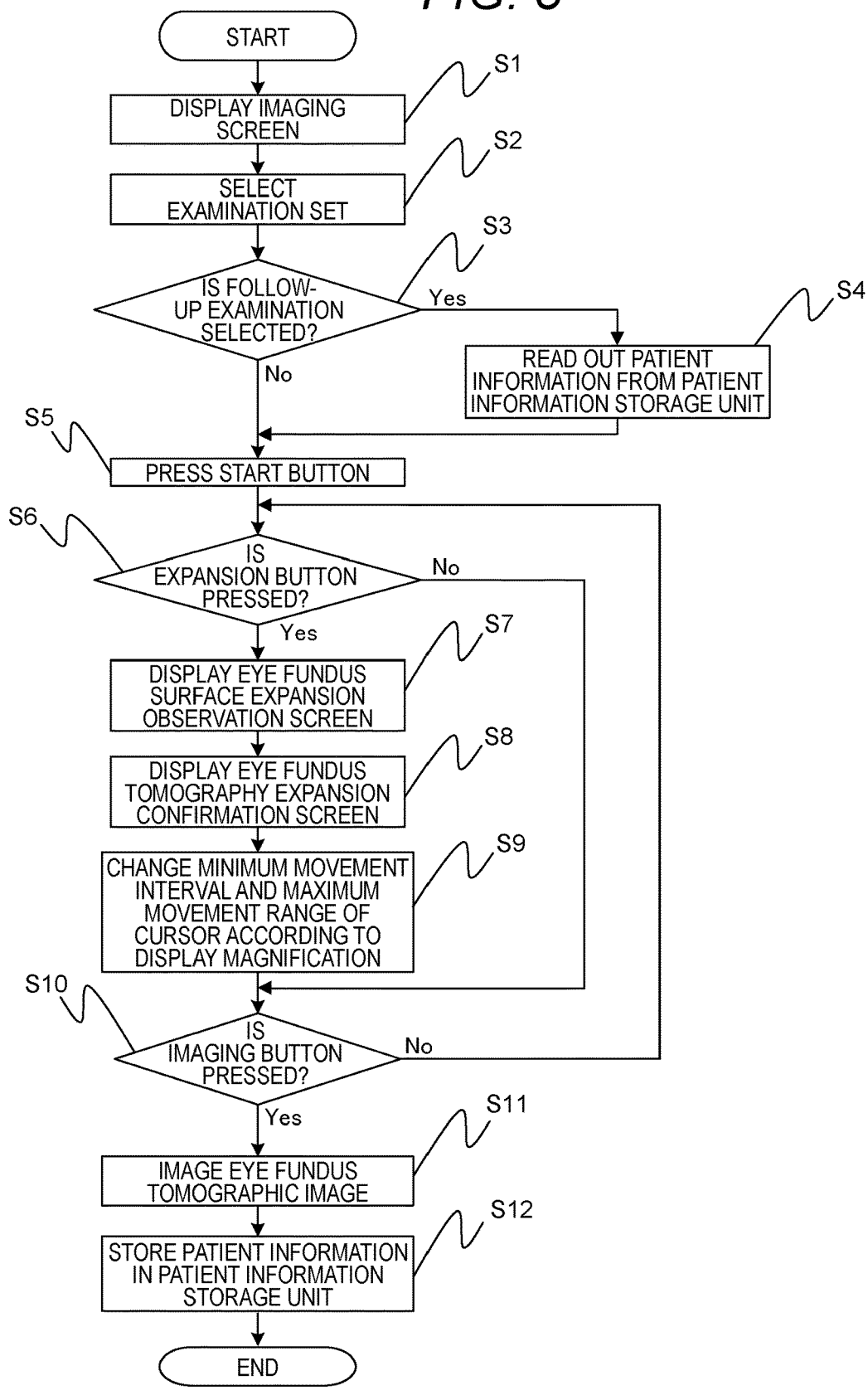
FIG. 3 is a flowchart illustrating imaging processing of eye fundus tomographic image data by an ophthalmological apparatus according to an embodiment of the present invention.

Next, processing of the computer 1003 of the ophthalmological apparatus 100 according to the present embodiment is described with reference to FIG. 3. Here, the processing illustrated in FIG. 3 denotes processing realized by reading out necessary data and program from a recording medium such as a ROM in the computer 1003 and executing them by the CPU.

In step S1, the computer 1003 displays the imaging screen 2000 on the monitor 1005. In step S2, the computer 1003 selects an examination set according to the examiner operation on the examination set selection screen 2010. In step S3, the computer 1003 determines whether a follow-up examination is selected. In a case where the follow-up examination is selected, the processing shifts to step S4. By contrast, in a case where the follow-up examination is not selected, the processing shifts to step S5.

In step S4, the computer 1003 reads out patient information from a patient information storage unit. The patient information includes a scan pattern group at the time of the past imaging processing, a scan position, a focus position, the existence/nonexistence of display and the display magnification of the eye fundus surface expansion observation screen 2204, and the existence/nonexistence of display and the display magnification of an eye fundus tomography expansion confirmation screen 2302. By performing the imaging processing based on the patient information, it is possible to newly acquire eye fundus tomographic image data of subject's eye E in a condition equal to that of eye fundus tomographic image data imaged in the past, which is a comparison target.

In step S5, the computer 1003 acquires eye fundus surface moving image data that is moving image data, according to the press of the start button 2004, and displays the eye fundus surface moving image data on the eye fundus surface observation screen 2201. The operator moves the cursor 2208 to a position in which eye fundus tomographic image data wants to be acquired, on the eye fundus surface moving image data displayed on the eye fundus surface observation screen 2201. By this means, moving image data that is the eye fundus tomographic image data corresponding to the position of the cursor 2208 is acquired and displayed on the eye fundus tomography confirmation screen 2301. Here, step S5 denotes a processing example of a surface moving image acquiring unit, a surface moving image display control unit, a tomographic image acquiring unit and a tomographic image display control unit.

In step S6, the computer 1003 determines whether the expansion button 2206 is pressed. For example, in a case where there is a small lesion in subject's eye E and it is difficult to specify the lesion area from the eye fundus surface moving image data, the operator presses the expansion button 2206. In a case where the expansion button 2206 is pressed, the processing shifts to step S7. By contrast, in a case where the expansion button 2206 is not pressed, the processing shifts to step S10.

In step S7, as illustrated in FIG. 2B, the computer 1003 expands the eye fundus surface moving image data displayed on the eye fundus surface observation screen 2201 and displays it on the eye fundus surface expansion observation screen 2204. Here, the eye fundus surface moving image data displayed on the eye fundus surface expansion observation screen 2204 denotes image data that expands an area enclosed by the alternate long and short dash line in the eye fundus surface moving image data displayed on the eye fundus surface observation screen 2201.

In step S8, as illustrated in FIG. 2B, the computer 1003 expands the eye fundus tomographic image data displayed on the eye fundus tomography confirmation screen 2301 and displays it on the eye fundus tomography expansion confirmation screen 2302. Here, the eye fundus tomographic image data displayed on the eye fundus tomography expansion confirmation screen 2302 denotes image data that expands an area enclosed by the alternate long and two short dashes line in the eye fundus tomographic image data displayed on the eye fundus tomography confirmation screen 2301. Here, steps S7 and S8 denote processing examples of a display magnification control unit.

The display magnification adjusted by the slider 2205 is displayed on an eye fundus surface display magnification displaying unit 2207 and an eye fundus tomography display magnification displaying unit 2304. Here, the display magnifications of the eye fundus surface moving image data and the eye fundus tomographic image data coordinate, and, for example, if the display magnification of the eye fundus surface moving image data is two times, the display magnification of the eye fundus tomographic image data is also two times.

In step S9, the computer 1003 also changes the minimum movement interval and maximum movement range of the cursor 2208 according to the display magnification. In the present embodiment, it is assumed that the minimum movement interval 10 um and the maximum movement range is 10 mm in a case where the display magnification is set to one time, and, in a case where the display magnification is set to two times, the minimum movement interval is changed to 5 um and the maximum movement range is changed to 5 mm. Moreover, the computer 1003 controls the movement of the cursor displayed on the eye fundus surface expansion observation screen 2204 according to the cursor 2208 such that the cursor 2208 displayed on the eye fundus surface observation screen 2201 and the cursor displayed on the eye fundus surface expansion observation screen 2204 coordinate and move. By this means, it is possible to improve the usability at the time of designating the imaging position of tomographic image data that is still image data. Here, step S9 denotes a processing example of a cursor movement distance control unit.

In step S10, the computer 1003 determines whether the imaging button 2003 is pressed. In a case where the imaging button 2003 is pressed, the processing shifts to step S11. By contrast, in a case where the imaging button 2003 is not pressed, the processing returns to step S6. Here, step S10 denotes a processing example of an accepting unit.

In step S11, the computer 1003 performs imaging processing of the eye fundus tomographic image data. By this means, the eye fundus tomographic image data that is still image data is imaged. In step S12, the computer 1003 stores, in the patient information storage unit, patient information such as the display magnification, the patient ID, and the imaging position at the time of the imaging processing of the current eye fundus tomographic image data. By this means, it is possible to perform imaging processing using the patient information stored this time at the time of the next follow-up imaging. Here, step S11 denotes a processing example of a tomographic image imaging unit. Moreover, step S12 denotes a processing example of a display magnification storage unit.

As described above, according to the present embodiment, since it is possible to expand and display eye fundus surface moving image data and eye fundus tomographic image data, it is possible to easily and accurately set the position of tomographic image data of eye fundus Er of subject's eye E to be imaged.

Also, although an ophthalmological apparatus that images eye fundus tomographic image data of the subject's eye has been described in the present embodiment, the present invention is not limited to this and is also applicable to an apparatus to image tomographic image data of other examination objects such as skin and internal organs. Moreover, although the optical head 1000 to image eye fundus tomographic image data and the computer 1003 are connected in a wired form such that communication is possible in the present embodiment, the optical head 1000 and the computer 1003 may be connected in a wireless form such that communication is possible.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like. While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-096981, filed May 2, 2013, which is hereby incorporated by reference herein in its entirety.

What is claimed is:
1. An ophthalmic imaging apparatus comprising:
a wavelength division member configured to cause wavelength division into an optical path for observation of a subject's eye and an optical path for an OCT optical system;
an illumination optical system provided in the optical path for observation of the subject's eye and configured to illuminate the subject's eye;
a sensor for observation of the subject's eye provided in the optical path for observation of the subject's eye and configured to detect returning light from the subject's eye illuminated by the illumination optical system;
a scanning unit provided in the optical path for the OCT optical system and configured to scan measurement light on the subject's eye;
an OCT sensor provided in the optical path for the OCT optical system and configured to detect interference light generated from reference light and returning light from the subject's eye illuminated by the measurement light;
a display control unit configured to display, on a displaying unit, (a) a first surface image that is a moving image showing a surface of the subject's eye and that is obtained using a signal output from the sensor for observation, (b) a first tomographic image that is a moving image showing a tomography of the subject's eye and that is obtained using a signal output from the

OCT sensor, and (c) a first line showing an acquisition position of the first tomographic image on the first surface image;

a control unit configured to control the scanning unit to scan the measurement light on a position in the subject's eye corresponding to a position of the first line changed in the first surface image in accordance with an operation performed by a user;

a display magnification control unit configured to control, according to an operation of an operator for one of the first surface image and the first tomographic image, a display magnification of the one of the first surface image and the first tomographic image in conjunction with controlling a display magnification of the other, wherein the display control unit displays, on the displaying unit, (a) a second surface image that is a moving image showing a surface of the subject's eye and that is obtained using the signal output from the sensor for observation and the controlled display magnification, (b) a second tomographic image that is a moving image showing a tomography of the subject's eye and that is obtained using the signal output from the OCT sensor and the controlled display magnification, and (c) a second line showing an acquisition position of the second tomographic image on the second surface image, wherein the control unit controls the scanning unit to scan measurement light on a position in the subject's eye corresponding to a position of the second line changed in the second surface image in accordance with an operation performed by a user, and wherein one of the position of the first line and the position of the second line is changed in conjunction with change of the other.

2. The ophthalmic imaging apparatus according to claim 1, wherein the second surface image is an expanded image of a part of the first surface image, and wherein the display control unit displays the expanded image on the displaying unit, a part of the expanded image being on a part of the first surface image.

3. The ophthalmic imaging apparatus according to claim 1, wherein the display magnification control unit controls the same display magnification of the second surface image and the second tomographic image, and wherein the display control unit displays, in conjunction with displaying an expanded one image of the first surface image and the first tomographic image, an expanded another image on the display unit based on the same display magnification.

4. The ophthalmic imaging apparatus according to claim 1, wherein the second tomographic image is an expanded image of a part of the first tomographic image, and wherein the display control unit displays the expanded image on the displaying unit, a part of the expanded image being on a part of the first tomographic image.

5. The ophthalmic imaging apparatus according to claim 1, wherein the second surface image is an expanded image of a part of the first surface image, and wherein the display control unit displays the first surface image and the expanded image on the displaying unit, further comprising a changing unit configured to change at least one of a movement interval and a movement range of the line.

6. The ophthalmic imaging apparatus according to claim 5, wherein the changing unit changes at least one of the movement interval and the movement range of the line so as to coordinate and move the first line in the first surface image and the second line in the second surface image.

7. The ophthalmic imaging apparatus according to claim 1, wherein the first surface image is an eye fundus surface image showing a surface of an eye fundus of the subject's eye, and the first tomographic image is an eye fundus tomographic image showing a tomography of the eye fundus of the subject's eye.

8. The ophthalmic imaging apparatus according to claim 1, further comprising:

an accepting unit configured to accept an imaging instruction in a state where the second surface image and the second tomographic image are displayed on the displaying unit; and an imaging unit configured to image a still image corresponding to the first tomographic image displayed on the displaying unit, according to acceptance of the imaging instruction in the acceptance unit.

9. The ophthalmic imaging apparatus according to claim 8, further comprising a display magnification storage unit configured to store patient information of the examination object including the controlled display magnification at a time of imaging processing of the still image corresponding to the first tomographic image in the imaging unit.

10. The ophthalmic imaging apparatus according to claim 9, wherein the still image corresponding to the first tomographic image displayed on the displaying unit is acquired, based on the display magnification which is previously stored by the display magnification storage unit and included in the patient information on the patient.

11. A control method of an ophthalmic imaging apparatus including a wavelength division member configured to cause wavelength division into an optical path for observation of a subject's eye and an optical path for an OCT optical system, an illumination optical system provided in the optical path for observation of the subject's eye and configured to illuminate the subject's eye, a sensor for observation of the subject's eye provided in the optical path for observation of the subject's eye and configured to detect returning light from the subject's eye illuminated by the illumination optical system, a scanning unit provided in the optical path for the OCT optical system and configured to scan measurement light on the subject's eye, an OCT sensor provided in the optical path for the OCT optical system and configured to detect interference light generated from reference light and returning light from the subject's eye illuminated by the measurement light, the control method comprising:

a step of displaying, on a displaying unit, (a) a first surface image that is a moving image showing a surface of the subject's eye and that is obtained using a signal output from the sensor for observation, (b) a first tomographic image that is a moving image showing a tomography of the subject's eye and that is obtained using a signal output from the OCT sensor, and (c) a first line showing an acquisition position of the first tomographic image on the first surface image;

a step of controlling the scanning unit to scan the measurement light on a position in the subject's eye corresponding to a position of the first line changed in the first surface image in accordance with an operation performed by a user;

a step of controlling, according to an operation of an operator for one of the first surface image and the first tomographic image, a display magnification of the one of the first surface image and the first tomographic image in conjunction with controlling a display magnification of the other;

a step of displaying, on the displaying unit, (a) a second surface image that is a moving image showing a surface of the subject's eye and that is obtained using the signal output from the sensor for observation and the controlled display magnification, (b) a second tomographic image that is a moving image showing a tomography of the subject's eye and that is obtained using the signal output from the OCT sensor and the controlled display magnification, and (c) a second line showing an acquisition position of the second tomographic image on the second surface image; and a step of controlling the scanning unit to scan measurement light on a position in the subject's eye corresponding to a position of the second line changed in the second surface image in accordance with an operation performed by a user, wherein one of the position of the first line and the position of the second line is changed in conjunction with change of the other.

12. The control method according to claim 11,
wherein the second surface image is an expanded image of a part of the first surface image, and
wherein the expanded image is displayed on a part of the first surface image on the displaying unit.

13. The control method according to claim 11,
wherein the same display magnification of the second surface image and the second tomographic image is controlled, and
wherein, in conjunction with displaying an expanded one image of the first surface image and the first tomographic image, an expanded another image is displayed on the display unit based on the same display magnification.

14. The control method according to claim 11,
wherein the second tomographic image is an expanded image of a part of the first tomographic image, and
wherein the expanded image is displayed on a part of the first tomographic image on the displaying unit.

15. A non-transitory computer-readable storage medium storing a program that causes a computer to execute each step of the control method according to claim 11.

16. An ophthalmic imaging apparatus comprising:
a wavelength division member configured to cause wavelength division into an optical path for observation of a subject's eye and an optical path for an OCT optical system;
an illumination optical system provided in the optical path for observation of the subject's eye and configured to illuminate the subject's eye;
a sensor for observation of the subject's eye provided in the optical path for observation of the subject's eye and configured to detect returning light from the subject's eye illuminated by the illumination optical system;
a scanning unit provided in the optical path for the OCT optical system and configured to scan measurement light on the subject's eye;
an OCT sensor provided in the optical path for the OCT optical system and configured to detect interference light generated from reference light and returning light from the subject's eye illuminated by the measurement light;

a display magnification control unit configured to control, according to operation of an operator for one of (a) a first surface image that is a moving image showing a surface of the subject's eye and that is obtained using a signal output from the sensor for observation and (b) a first tomographic image that is a moving image showing a tomography of the subject's eye and that is obtained using a signal output from the OCT sensor, a display magnification of the one in conjunction with controlling a display magnification of the other;

a display control unit configured to display, on the displaying unit, (a) a second surface image that is a moving image showing a surface of the subject's eye and that is obtained using the signal output from the sensor for observation and the controlled display magnification, (b) a second tomographic image that is a moving image showing a tomography of the subject's eye and that is obtained using the signal output from the OCT sensor and the controlled display magnification and (c) a line showing an acquisition position of the second tomographic image on the second surface image; and a control unit configured to control the scanning unit to scan the measurement light on a position in the subject's eye corresponding to a position of the line changed in the second surface image in accordance with an operation performed by a user.

17. A control method of an ophthalmic imaging apparatus including a wavelength division member configured to cause wavelength division into an optical path for observation of a subject's eye and an optical path for an OCT optical system, an illumination optical system provided in the optical path for observation of the subject's eye and configured to illuminate the subject's eye, a sensor for observation of the subject's eye provided in the optical path for observation of the subject's eye and configured to detect returning light from the subject's eye illuminated by the illumination optical system, a scanning unit provided in the optical path for the OCT optical system and configured to scan measurement light on the subject's eye, an OCT sensor provided in the optical path for the OCT optical system and configured to detect interference light generated from reference light and returning light from the subject's eye illuminated by the measurement light, the control method comprising:
a step of controlling, according to operation of an operator for one of (a) a first surface image that is a moving image showing a surface of the subject's eye and that is obtained using a signal output from the sensor for observation and (b) a first tomographic image that is a moving image showing a tomography of the subject's eye and that is obtained using a signal output from the OCT sensor, a display magnification of the one in conjunction with controlling a display magnification of the other;

a step of displaying, on the displaying unit, (a) the second surface image that is a moving image showing a surface of the subject's eye and that is obtained using the signal output from the sensor for observation and the controlled display magnification, (b) the second tomographic image that is a moving image showing a tomography of the subject's eye and that is obtained using the signal output from the OCT sensor and the controlled display magnification and (c) a line showing an acquisition position of the second tomographic image on the second surface image; and a step of controlling the scanning unit to scan the measurement light on a position in the subject's eye corresponding to a position of the line changed in the second surface image in accordance with an operation performed by a user.

18. A non-transitory computer-readable storage medium storing a program that causes a computer to execute each step of the control method according to claim 17.

19. The ophthalmic imaging apparatus according to claim 16, wherein the display magnification control unit controls the same display magnification of the second surface image and the second tomographic image, and wherein the display control unit displays, in conjunction with displaying an expanded one image of the first surface image and the first tomographic image, an expanded another image on the display unit based on the same display magnification.

* * * * *